(12) United States Patent
Sugiyama et al.

(10) Patent No.: US 11,266,771 B2
(45) Date of Patent: Mar. 8, 2022

(54) CONCENTRATION MEASURING MODULE, DIALYZER, AND CONCENTRATION CALCULATING METHOD

(71) Applicant: ASAHI KASEI KABUSHIKI KAISHA, Tokyo (JP)

(72) Inventors: Sho Sugiyama, Tokyo (JP); Shinji Miya, Tokyo (JP); Yoshiro Yamaha, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 747 days.

(21) Appl. No.: 16/034,569

(22) Filed: Jul. 13, 2018

(65) Prior Publication Data
US 2019/0015573 A1    Jan. 17, 2019

(30) Foreign Application Priority Data

Jul. 14, 2017 (JP) .............................. JP2017-138412
Jun. 13, 2018 (JP) .............................. JP2018-112777

(51) Int. Cl.
*A61M 1/16* (2006.01)
*A61B 5/00* (2006.01)
(Continued)

(52) U.S. Cl.
CPC ......... *A61M 1/1609* (2014.02); *A61B 5/0071* (2013.01); *A61B 5/1455* (2013.01);
(Continued)

(58) Field of Classification Search
CPC .............. A61M 1/1609; A61M 1/1619; A61M 2202/0498
See application file for complete search history.

(56) References Cited

U.S. PATENT DOCUMENTS 4,698,308 A    10/1987 Ikeda
6,666,840 B1   12/2003 Falkvall et al.
(Continued)

FOREIGN PATENT DOCUMENTS

JP    S61186854 A    8/1986
JP    2002-516722 A  6/2002
(Continued)

OTHER PUBLICATIONS

European Search Report dated Nov. 30, 2018 for application No. 18183104.1, 4 pages.

*Primary Examiner* — Leslie R Deak
(74) *Attorney, Agent, or Firm* — Morgan, Lewis & Bockius LLP

(57) ABSTRACT

To provide a concentration calculating module configured to measure the concentrations of two constituents simultaneously with higher accuracy.
The concentration measuring module includes a light source configured to emit light into a housing; a first light receiving unit configured to have sensitivity to a wavelength of output light of the light source and receive light radiated from inside the housing; and a second light receiving unit configured to have sensitivity to a longer wavelength than the first light receiving unit and receive light radiated from inside the housing. The light source, the first light receiving unit, and the second light receiving unit are arranged to have a positional relationship in which a light emitting surface of the light source faces a light receiving surface of the first light receiving unit, and a normal to a light receiving surface of the second light receiving unit is orthogonal to, of a line through the light source and the first light receiving unit, a line segment corresponding to the inside of the housing, and a length X of, of the line through the light source and the first light receiving unit, the line segment corresponding to the inside of the housing and then a length Y of, of a line
(Continued)

including the normal to the light receiving surface of the second light receiving unit, a line segment corresponding to the inside of the housing satisfy Y/X>1. The concentration measuring module calculates the concentrations of two constituents simultaneously on the basis of first and second signals output from the first and second light receiving units.

21 Claims, 10 Drawing Sheets

(51) Int. Cl.
  *A61B 5/1455* (2006.01)
  *A61M 1/36* (2006.01)
  *A61B 5/145* (2006.01)

(52) U.S. Cl.
  CPC ....... *A61B 5/14546* (2013.01); *A61M 1/1619* (2014.02); *A61B 5/6887* (2013.01); *A61B 2560/0406* (2013.01); *A61B 2562/182* (2013.01); *A61M 1/3609* (2014.02); *A61M 2202/0498* (2013.01); *A61M 2205/15* (2013.01); *A61M 2205/3313* (2013.01)

(56) References Cited

U.S. PATENT DOCUMENTS

| | | | |
|---|---|---|---|
| 2010/0327184 A1* | 12/2010 | Hayashi | G01N 15/1436 250/459.1 |
| 2013/0010537 A1 | 1/2013 | Kawai et al. | |
| 2014/0098359 A1* | 4/2014 | Gross | A61B 5/14546 356/36 |
| 2014/0263064 A1* | 9/2014 | Jones | A61M 1/1609 210/647 |
| 2016/0064117 A1 | 3/2016 | Romero et al. | |

FOREIGN PATENT DOCUMENTS

| | | |
|---|---|---|
| JP | 2014518517 A | 7/2014 |
| JP | 2015-146837 A | 8/2015 |
| JP | 2016000125 A | 1/2016 |
| WO | 2012/140022 A1 | 10/2012 |
| WO | 2013/141309 A1 | 9/2013 |

* cited by examiner

F I G. 14

| | URIC ACID CONCENTRATION (mg/dL) | ALBUMIN CONCENTRATION (mg/dL) | OUTPUT SIGNAL FROM FIRST LIGHT RECEIVING UNIT (ABSORPTION COEFFICIENT) | OUTPUT SIGNAL FROM SECOND LIGHT RECEIVING UNIT FLUORESCENCE INTENSITY $FI(a.u.)$ | CORRECTED FLUORESCENCE INTENSITY $FI norm(a.u.)$ |
|---|---|---|---|---|---|
| CONDITION 1 | 0 | 32 | 0.20 | 144 | 155 |
| CONDITION 2 | 1 | 32 | 0.73 | 118 | 153 |
| CONDITION 3 | 2 | 32 | 1.26 | 102 | 157 |
| CONDITION 4 | 4 | 32 | 2.29 | 76 | 158 |
| CONDITION 5 | 8 | 32 | 4.29 | 51 | 164 |
| CONDITION 6 | 0 | 16 | 0.11 | 72 | 75 |
| CONDITION 7 | 1 | 16 | 0.63 | 56 | 70 |
| CONDITION 8 | 2 | 16 | 1.16 | 48 | 71 |
| CONDITION 9 | 4 | 16 | 2.20 | 34 | 69 |
| CONDITION 10 | 8 | 16 | 4.23 | 24 | 76 |
| CONDITION 11 | 0 | 8 | 0.05 | 34 | 35 |
| CONDITION 12 | 1 | 8 | 0.59 | 27 | 34 |
| CONDITION 13 | 2 | 8 | 1.12 | 23 | 34 |
| CONDITION 14 | 4 | 8 | 2.15 | 17 | 34 |
| CONDITION 15 | 8 | 8 | 4.19 | 11 | 34 | ized dialysis membrane capable of
CONCENTRATION MEASURING MODULE, DIALYZER, AND CONCENTRATION CALCULATING METHOD

BACKGROUND OF THE INVENTION

Field of the Invention

The present invention relates to a concentration measuring module, a dialyzer, and a concentration calculating method.

Description of the Related Art

There are various kinds of dialysis treatment as blood processing to cleanse the blood of a patient who has lost his/her kidney function due to renal failure or the like, instead of the patient's kidneys. These kinds of dialysis treatment include hemodialysis treatment to circulate a patient's blood through an extracorporeal circuit and excrete wastes in the blood into dialysate that is separated by a dialysis membrane and is circulated through another circuit. In such hemodialysis treatment, there is known spent dialysate monitoring in which wastes that has been excreted from a patient's blood and dissolved in spent dialysate are monitored over time to grasp the degree of progress of dialysis.

As a method of spent dialysate monitoring, there has been proposed a method of measuring wastes in spent dialysate on the basis of the transmittance of ultraviolet light through the spent dialysate (for example, see PTL 1).

Meanwhile, if dialysis treatment is prolonged, a patient may develop complications, such as dialysis amyloidosis resulting from β2-microglobulin deposition. It is known that the symptoms of dialysis amyloidosis can be alleviated by using a highly permeable dialysis membrane capable of removing low molecular weight protein. However, such a highly permeable dialysis membrane is also highly permeable to other substances, and therefore also leaks, for example, albumin needed by the body at the same time.

Accordingly, in PTL 2, to optimize an amount of albumin leakage in one-time dialysis treatment, calculation of a predictive value of the amount of clinical albumin leakage and calculation of a dialysis condition for obtaining a target amount of albumin leakage are performed.

To perform appropriate dialysis using a highly permeable dialysis membrane, it is necessary to perform continuous real-time monitoring of the concentrations of a urea-like solute and albumin, which are wastes in spent dialysate, simultaneously. Accordingly, there has been proposed a method of measuring the permeabilities of a fraction containing albumin and a fraction containing no albumin separately by means of a filter and calculating its difference as albumin concentration (for example, see PTL 3). Furthermore, there has also been proposed a method of providing a plurality of light receiving units and monitoring the intensity of transmitted light and the intensity of fluorescence, thereby continuously monitoring the concentrations of a urea-like solute and albumin simultaneously (for example, see PTL 4).

CITATION LIST

Patent Literature

PTL 1: JP 2002-516722 T
PTL 2: WO 2013/141309
PTL 3: JP 2015-146837 A
PTL 4: WO 2012/140022

SUMMARY OF THE INVENTION

However, in the method described in PTL 4, there is stray light due to diffused reflection from the surface of a light source, and there remains room for improvement in the accuracy of measurement of the concentrations of two constituents.

Accordingly, the present invention is intended to provide a concentration measuring module, a dialyzer, and a concentration calculating method that are capable of measuring the concentrations of two constituents contained in fluid simultaneously with higher accuracy.

A concentration measuring module according to an aspect of the present invention includes a housing configured to be able to house an irradiated body; a light source configured to emit light into the housing; a first light receiving unit configured to have sensitivity to a wavelength of output light of the light source and receive light radiated from inside the housing; and a second light receiving unit configured to have sensitivity to a longer wavelength than the first light receiving unit and receive light radiated from inside the housing. The light source and the first light receiving unit are arranged so that a light emitting surface of the light source faces a light receiving surface of the first light receiving unit. The light source, the first light receiving unit, and the second light receiving unit are arranged to have a positional relationship in which a normal to a light receiving surface of the second light receiving unit is orthogonal to, of a line through the light source and the first light receiving unit, a line segment corresponding to the inside of the housing. A length X of, of the line through the light source and the first light receiving unit, the line segment corresponding to the inside of the housing and a length Y of, of a line including the normal to the light receiving surface of the second light receiving unit, a line segment corresponding to the inside of the housing satisfy Y/X>1.

A dialyzer according to another aspect of the present invention includes the concentration measuring module according to the above-described aspect.

Furthermore, a concentration calculating method to still another aspect of the present invention is a method of calculating the concentrations of two constituents contained in an irradiated body irradiated with output light of a light source by using the concentration measuring module according to the above-described aspect. The concentration calculating method includes acquiring a first signal correlated to an amount of absorption of the output light by the irradiated body; acquiring a second signal correlated to an amount of excitation of the irradiated body by the output light, the second signal being different from the first signal; and calculating the concentrations of the two constituents on a basis of the first and second signals.

According to an aspect of the present invention, it is possible to measure the concentrations of two constituents contained in fluid simultaneously with higher accuracy.

BRIEF DESCRIPTION OF THE DRAWINGS

FIG. 14 is an example of results of detection of the absorption coefficient and the fluorescence intensity when the uric acid concentration and the albumin concentration were changed.

DESCRIPTION OF THE PREFERRED EMBODIMENTS

Figure 1:
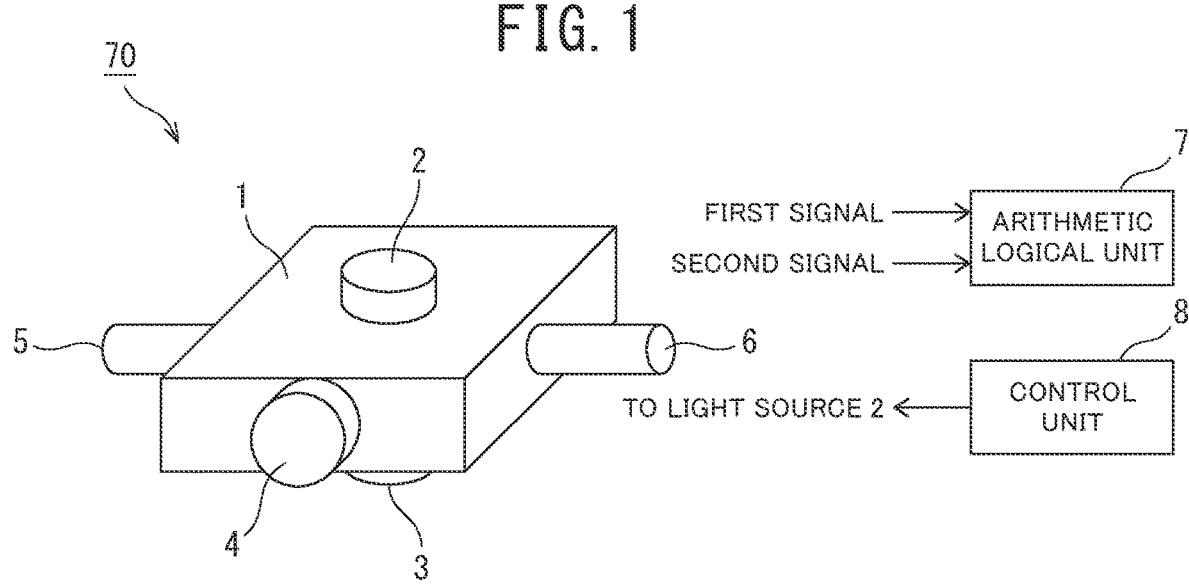
FIG. 1 is a conceptual diagram illustrating a configuration of a concentration measuring module according to an embodiment of the present invention.

Embodiments of the present invention will be described below with reference to drawings. Components corresponding to each other in the drawings are assigned the same reference numeral, and description of the duplicated component is appropriately omitted. Furthermore, the embodiments described below are just examples of configurations in which the technical ideas of the invention are embodied, and do not mean to specify the material, shape, structure, arrangement, dimensions, etc. of each component. Various modifications can be made to the technical ideas of the invention within the technical scope defined by claims described herein.

[Concentration Measuring Module]

A concentration measuring module according to an embodiment of the present invention includes a housing that can house an irradiated body and a light source that emits light into the housing. The concentration measuring module further includes first and second light receiving units that receive light radiating from inside the housing. The first light receiving unit has sensitivity to a wavelength of the light emitted from the light source (hereinafter, referred to as the output light of the light source or simply as the output light). The second light receiving unit has sensitivity to a longer wavelength than the first light receiving unit.

A portion of the output light of the light source enters the irradiated body and is partially absorbed by the irradiated body, and then enters the first light receiving unit. Since the first light receiving unit has sensitivity to the wavelength of the output light of the light source, the first light receiving unit generates an electrical signal (hereinafter, also referred to as a first signal) according to the transmittance of the irradiated body with respect to the wavelength of the output light. Therefore, the concentration of a light-absorbing solute in the irradiated body can be calculated on the basis of the first signal. For example, the concentration of a urea-like solute as an example of the light-absorbing solute can be measured.

Furthermore, the portion of the output light that has entered the irradiated body excites a fluorescent substance contained in the irradiated body. The excited fluorescent substance radiates lower-energy light than the output light, i.e., longer-wavelength light than the output light. A portion of the light radiated from the fluorescent substance enters the second light receiving unit. Since the second light receiving unit has sensitivity to a longer wavelength than the first light receiving unit, the second light receiving unit generates an electrical signal (hereinafter, also referred to as a second signal) according to the light that the fluorescent substance radiates. Therefore, the concentration of a fluorescent solute in the irradiated body can be calculated on the basis of the second signal. For example, the concentration of albumin as an example of the fluorescent solute can be measured.

Consequently, the concentration measuring module according to the present embodiment can measure the concentrations of two constituents contained in an irradiated body simultaneously.

Furthermore, the light source and the first light receiving unit are arranged so that a light emitting surface of the light source faces a light receiving surface of the first light receiving unit, and the light source and the first and second light receiving units are arranged so as to have a positional relationship in which a normal to a light receiving surface of the second light receiving unit is orthogonal to, of a line through the light source and the first light receiving unit, a line segment corresponding to the inside of the housing and to satisfy "Y/X>1", where X denotes the length of, of the line through the light source and the first light receiving unit, the line segment corresponding to the inside of the housing; Y denotes the length of, of a line including the normal to the light receiving surface of the second light receiving unit, a line segment corresponding to the inside of the housing. Accordingly, it is possible to further reduce the effect of stray light.

[Dialyzer]

A dialyzer according to another embodiment of the present invention is a dialyzer including the above-described concentration measuring module.

The dialyzer according to the present embodiment can continuously monitor two constituents contained in spent dialysate simultaneously.

[Concentration Calculating Method]

A concentration calculating method according to still another embodiment of the present invention is a method to calculate the concentrations of two constituents contained in an irradiated body irradiated with output light of a light source by using the above-described concentration measuring module. The concentration calculating method includes acquiring a first signal correlated to the amount of absorption of output light of the light source that has been adsorbed by the irradiated body; acquiring a second signal correlated to the amount of excitation of the irradiated body by the output light; and calculating the concentrations of two constituents on the basis of the first and second signals. By acquiring the first and second signals from the irradiated body, the concentrations of two constituents contained in the irradiated body can be measured simultaneously.

Subsequently, components of the concentration measuring module according to the embodiment of the present invention are described.

[Housing]

The housing included in the concentration measuring module can house an irradiated body. The housing is configured to allow an output light from the light source provided outside the housing to enter inside the housing, or is made of a material that allows the output light to enter inside the housing. Furthermore, the housing is configured to allow a portion of the output light that has entered inside the housing to enter the first light receiving unit provided outside the housing, or is made of a material that allows the portion of the output light to enter the first light receiving unit. Moreover, the housing is configured to allow a portion of light that a fluorescent substance in the irradiated body radiates to enter the second light receiving unit provided outside the housing, or is made of a material that allows the portion of the light radiated from the fluorescent substance to enter the second light receiving unit. Specifically, for example, some portions of the housing, i.e., a portion that faces the light emitting surface of the light source, a portion that faces the light receiving surface of the first light receiving unit, and a portion that faces the light receiving surface of the second light receiving unit may be made of a material that allows the output light to pass therethrough. Incidentally, the first and second light receiving units do not always have to be provided outside the housing, and may be provided, for example, inside the housing, as long as they can receive, of the output light, light attenuated by the irradiated body or excitation light of the irradiated body excited by the output light.

Examples of the material that allows the output light to pass therethrough may include soda-lime glass, borosilicate glass, quartz glass, crystal, sapphire, diamond, spinel, yttrium-stabilized zirconia, and SiC; however, the material is not particularly limited to these, and various materials can be used depending on the wavelength of the output light. In a case where the output light is ultraviolet light, for example, quartz glass or sapphire is preferably used as the material of the housing.

Furthermore, the housing is preferably provided with an irradiated body inlet through which an irradiated body can be introduced into the housing and an irradiated body outlet through which the irradiated body is discharged from the housing. The housing may be configured to be provided with through holes as an example of the irradiated body inlet and the irradiated body outlet.

Moreover, the irradiated body introduced into the housing is preferably made of two or more constituents. Then, the irradiated body made of two or more constituents makes it possible to measure the concentrations of two constituents contained in the irradiated body on the basis of first and second signals.

[Light Source]

The light source included in the concentration measuring module is installed outside or inside the housing so that an irradiated body is irradiated with light output from the light source (output light). A wavelength band of the output light may be any band of wavelength as long as the band of wavelength is absorbed by, of the two or more constituents contained in the irradiated body, one of two constituents set as objects of concentration measurement and can excite the other constituent. The light source does not always have to be provided outside the housing, and may be provided inside the housing.

From the perspective of increasing the intensity of excitation light and improving the S/N ratio of a second signal that is an output of the second light receiving unit, preferably, the light source particularly emits light with a wavelength band of 200 nm or more and 300 nm or less. If the wavelength band of light emitted from the light source is less than 200 nm, the light is absorbed by superficial part of the irradiated body, and sufficient fluorescence may not be obtained. If the wavelength band of light emitted from the light source is more than 300 nm, it may become difficult to separate a wavelength of fluorescence of protein, one of measuring objects in the irradiated body, from another light component such as scattered light. That is, the S/N ratio may be declined.

As an example of the light source that emits light with a wavelength band of 200 nm or more and 300 nm or less, a light source whose light emitting element (LED) has a light emitting layer with a band gap of, for example, 4.13 eV or more can be used. More specifically, a light source having a structure of p-n junction, p-i-n junction, or single or double heterojunction using gallium nitride (GaN) or aluminum gallium nitride (AlGaN) as a light emitting layer or a structure in which a multiquantum well structure is introduced into the above structure can be used.

Furthermore, as another example of the light source that emits light with a wavelength band of 200 nm or more and 300 nm or less, a mercury lamp can also be used.

Moreover, from the perspective of letting output light be single-wavelength light and improving the measurement accuracy, the light source preferably has an optical element such as a bandpass filter.

Furthermore, from the perspective of preventing unwanted reflected light or the like from entering the first and second light receiving units, the light source preferably has a barrier that imposes a limitation on the emission angle of the output light.

[First Light Receiving Unit]

The first light receiving unit included in the concentration measuring module may be any light receiving element as long as it has sensitivity to the wavelength of light output from the light source (output light). The sensitivity here means the ability to convert incident light into an electrical signal. That is, the first light receiving unit may be any light receiving element as long as it can output an electrical signal when having received light corresponding to the wavelength of the output light.

Furthermore, the first light receiving unit preferably receives light radiated from inside to outside the housing, of the output light. This enables the first light receiving unit to detect absorption of the output light by a constituent contained in the irradiated body.

Moreover, the first light receiving unit preferably receives light of a wavelength attenuated by the irradiated body, of the output light. This enables the first light receiving unit to output, as a first signal, a signal depending on the concentration of a constituent that absorbs the output light, of constituents contained in the irradiated body.

Furthermore, the first light receiving unit may receive light of a wavelength attenuated by uric acid that is one of urea-like substances contained in the irradiated body, of the output light. Since uric acid exhibits strong absorption of light of a wavelength of about 280 nm or more and 300 nm or less, an ultraviolet light-emitting diode (LED) can be used as the light source. In this case, as will be described later, albumin is highly excited by light of 280 nm; therefore, in a case where the irradiated body contains uric acid and albumin, the concentrations of the both constituents can be measured simultaneously with high accuracy.

The first signal output from the first light receiving unit may be output to, for example, an arithmetic logical unit to be described later. Alternatively, the first signal output from the first light receiving unit may be output to a control unit that controls the light source, and the control unit may perform arithmetic processing.

Various light receiving elements can be used as the first light receiving unit. The various light receiving elements include, for example, a photodiode. In a case where a photodiode is used as the first light receiving unit, since the first light receiving unit has sensitivity to the wavelength of the output light, a light receiving layer of the photodiode can be made of a semiconductor material that allows the light receiving layer to have a band gap equal to or smaller than energy of the wavelength of the output light. More specifically, a light receiving element having a structure of a general photodiode, a Schottky photodiode using only either a p- or n-type conductive layer, an MSM photodiode, a phototransistor, or a photoconductor can be used as the first light receiving unit; however, the first light receiving unit is not limited to this.

Furthermore, from the perspective of letting light that enters the first light receiving unit be single-wavelength light and improving the measurement accuracy, the first light receiving unit preferably has an optical element such as a bandpass filter.

Moreover, from the perspective of preventing unwanted reflected light or the like from entering the first light receiving unit, the first light receiving unit preferably has a barrier that imposes a limitation on the incident angle of incident light.

[Second Light Receiving Unit]

The second light receiving unit included in the concentration measuring module may be any light receiving element as long as it has sensitivity to a longer wavelength than the first light receiving unit. The sensitivity here means the ability to convert incident light into an electrical signal. Furthermore, "the second light receiving unit has sensitivity to a longer wavelength than the first light receiving unit" here means that a wavelength at which the output of the second light receiving unit reaches its peak is longer than a wavelength at which the output of the first light receiving unit reaches its peak.

Moreover, the second light receiving unit preferably receives light radiated from inside to outside the housing, of the output light. This enables the second light receiving unit to detect excitation of a constituent contained in the irradiated body by the output light.

Furthermore, the second light receiving unit preferably has sensitivity to excitation light that the irradiated body excited by the output light radiates and has a longer wavelength than the output light. This enables the second light receiving unit to output, as a second signal, a signal depending on the concentration of a constituent excited by the output light, of constituents contained in the irradiated body.

Moreover, the second light receiving unit may receive excitation light that albumin contained in the irradiated body radiates when irradiated with the output light. Since albumin is highly excited by light of 280 nm, an LED can be used as the light source. Furthermore, in this case, as described above, uric acid strongly absorbs light of a wavelength of 280 nm; therefore, in a case where the irradiated body contains uric acid and albumin, the concentrations of the both constituents can be measured simultaneously with high accuracy.

The second signal output from the second light receiving unit may be output to, for example, the arithmetic logical unit to be described later. Alternatively, the second signal may be output to the control unit that controls the light source, and the control unit may perform arithmetic processing for detecting the concentrations.

Various light receiving elements can be used as the second light receiving unit. The various light receiving elements include, for example, a photodiode. In a case where a photodiode is used as the second light receiving unit, since the second light receiving unit has sensitivity to the wavelength of the output light, a light receiving layer of the photodiode can be made of a semiconductor material that allows the light receiving layer to have a band gap equal to or smaller than energy of the wavelength of the output light.

More specifically, a light receiving element having a structure of a general photodiode, a Schottky photodiode using only either a p- or n-type conductive layer, an MSM photodiode, a phototransistor, or a photoconductor can be used as the second light receiving unit; however, the second light receiving unit is not limited to this.

Furthermore, from the perspective of letting light that enters the second light receiving unit be single-wavelength light and improving the measurement accuracy, the second light receiving unit preferably has an optical element such as a bandpass filter.

Moreover, from the perspective of preventing unwanted reflected light or the like from entering the second light receiving unit, the second light receiving unit preferably has a barrier that imposes a limitation on the incident angle of incident light.

The second light receiving unit included in the concentration measuring module may be any light receiving element as long as it receives fluorescence from an irradiated body irradiated with light from a light source, and photoelectrically converts the fluorescence into an electrical signal and outputs the electrical signal.

The electrical signal (the second signal) output from the second light receiving unit can be input to, for example, the control unit that controls the light source. Furthermore, to enable the second light receiving unit to output an electrical signal according to incident light, a light receiving layer of a light receiving element (for example, a photodiode) included in the second light receiving unit may be a semiconductor that allows the light receiving layer to have a band gap equal to or smaller than energy of incident light. Specifically, the second light receiving unit may have a structure of a photodiode, a Schottky photodiode using only either a p- or n-type conductive layer, an MSM photodiode, a phototransistor, or a photoconductor.

Moreover, an optical element, such as a bandpass filter, or a barrier that imposes a limitation on the emission angle can be interposed between the second light receiving unit and the housing as needed.

Since the electrical signal (the second signal) output from the second light receiving unit is a very weak signal, the electrical signal output from the second light receiving unit may be amplified by an amplifier circuit. In this case, to make a distinction between a current of the electrical signal and a noise current generated due to vibration of wiring, an external electric field, or the like, the distance from a photoreceptor of the second light receiving unit to the first amplifier circuit, i.e., the distance in a straight line between the center of a photoreceptor of the second light receiving unit and a point at which wiring is in contact with the first amplifier circuit (hereinafter, also referred to as the inter-circuit straight-line distance) is preferably 5 cm or less, more preferably 2 cm or less.

The amplifier circuit is preferably one that converts weak current into voltage and amplifies this voltage by a predetermined gain; however, a conversion circuit that converts current into voltage as needed and converts the voltage into a frequency can also be used instead of the amplifier circuit. In a case where the amplifier circuit is provided, wiring from the photoreceptor of the second light receiving unit to the first amplifier circuit is preferably covered with a good conductor, more preferably covered with metal, and most preferably covered with aluminum or copper.

Furthermore, the concentration measuring module and the entire amplifier circuit of the second light receiving unit are preferably covered with a good conductor of electricity, and, to practically cover them with a good conductor, 90% or more of a solid angle viewed from the center of wiring is preferably covered with the good conductor. The term "the center of wiring" here is position M illustrated in FIG. 9 to be described later, and means the weight center of a conductor of an electric wire used in wiring.

By covering the part very sensitive to noise from the photoreceptor of the second light receiving unit to the first amplifier circuit with the good conductor, the first amplifier circuit is electrically shielded, and it is possible to prevent an external electric field from generating a noise current. The electric shielding is achieved by electrically connecting the ground potential of the first amplifier circuit to the good conductor used to cover. Incidentally, the first amplifier circuit here is an amplifier circuit to which an electrical signal that has been output from the second light receiving unit and has not been amplified by any amplifier circuit is input. For example, in a case where an electrical signal output from the second light receiving unit is configured to be sequentially amplified by a plurality of amplifier circuits connected in multiple stages, the first amplifier circuit means the first-stage amplifier circuit. Furthermore, the photoreceptor means a component that outputs a signal according to the intensity of incident light, of components such as light receiving elements included in the second light receiving unit.

[Positional Relationship of Light Source, First Light Receiving Unit, and Second Light Receiving Unit]

The concentration measuring module according to the embodiment of the present invention preferably satisfies "$1 \leq Q/P \leq 200$", where P denotes the view volume of the first light receiving unit with respect to the inside of the housing, and Q denotes the view volume of the second light receiving unit with respect to the inside of the housing. By reducing the view volume P, excitation light required for measurement can be obtained even in a case where the absorbance of an irradiated body is high. By increasing the view volume Q, the number of photons incident on the second light receiving unit is increased, and fluorescence can efficiently enter photodiodes provided as the first and second light receiving units. If Q/P is smaller than 1, a new optical system or a large-scale electric amplification mechanism may be required to measure fluorescence with a lower intensity than transmitted light. If Q/P is larger than 200, the second light receiving unit becomes far away from the light source, and may have a shape that makes it difficult to maintain a light path stably.

Here, the definition of the view volume P of the first light receiving unit is described. First, a view angle of the first light receiving unit is determined by an arrangement relationship of the housing and the first light receiving unit, a material of the housing, the shape of a light incident surface of the first light receiving unit, etc. A total view area obtained by adding up all view areas that the first light receiving unit has with respect to an internal space of the housing on the basis of this view angle is defined as the view volume P. The view volume Q of the second light receiving unit is defined in the same manner as described above.

Figure 2:
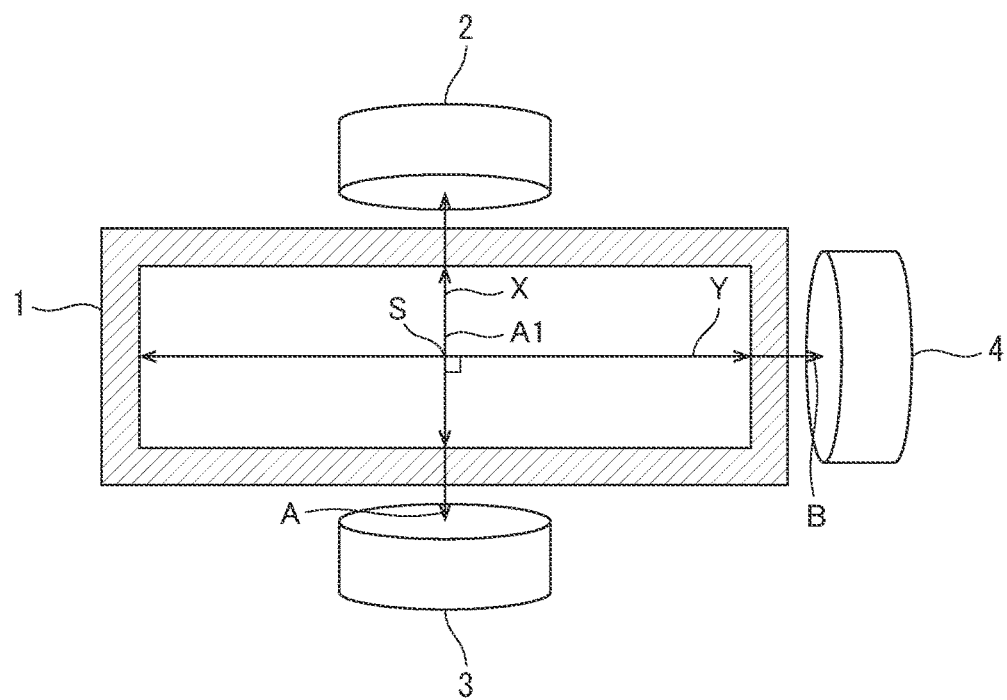
FIG. 2 is a cross-sectional view illustrating the configuration of the concentration measuring module illustrated in FIG. 1.

The second light receiving unit included in the concentration measuring module according to the embodiment of the present invention is preferably arranged so that a line B substantially perpendicular to a line segment A1 belonging to the inside of the housing coincides with a normal to the light receiving surface of the second light receiving unit, of a line segment A connecting the light source with the first light receiving unit as illustrated in a cross-sectional view of the housing in FIG. 2. By arranging the second light receiving unit in this way, noise due to a stray light component of output light of the light source can be minimized.

Furthermore, in this case, the line B preferably passes through a midpoint S of the line segment A1. That is, the second light receiving unit is preferably arranged so that a normal passing through the center of the light receiving surface of the second light receiving unit forms part of the line B. By arranging the second light receiving unit in this way, light from a portion of high fluorescence emission is more likely to enter the second light receiving unit.

Moreover, in this case, a length X of the line segment A1 preferably satisfies "$1 \text{ mm} \leq X \leq 10 \text{ mm}$". If X is shorter than 1 mm, the meniscus force of liquid increases, and it is necessary to provide an additional part such as a straightening plate for uniformly distributing the irradiated body. If X is longer than 10 mm, it becomes difficult to control the convection of the irradiated body inside the housing, and it is still necessary to provide an additional part such as a straightening plate.

Figure 3:
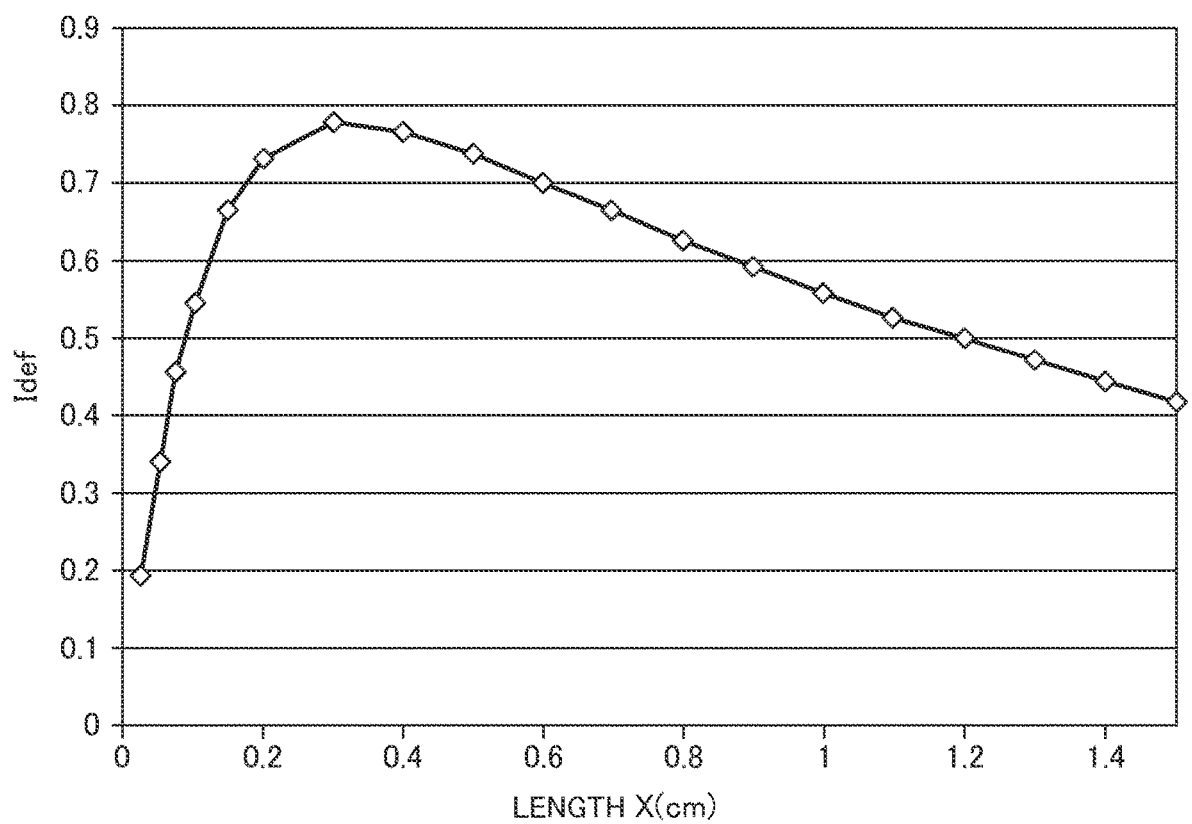
FIG. 3 is an example of a characteristic diagram illustrating a relationship between a length X of, of a line through a light source and a first light receiving unit, a portion corresponding to the inside of a housing and Idef.

Furthermore, as illustrated in a graph in FIG. 3, the length X of the line segment A1 more preferably satisfies "$2 \text{ mm} \leq X \leq 5 \text{ mm}$". If X is shorter than 2 mm, the transmittance becomes too high, and sufficient excitation light is not obtained. If X is longer than 5 mm, the absorbance may become too high, and a light source having very high irradiation intensity may be required for the measurement of transmittance.

Figure 5:
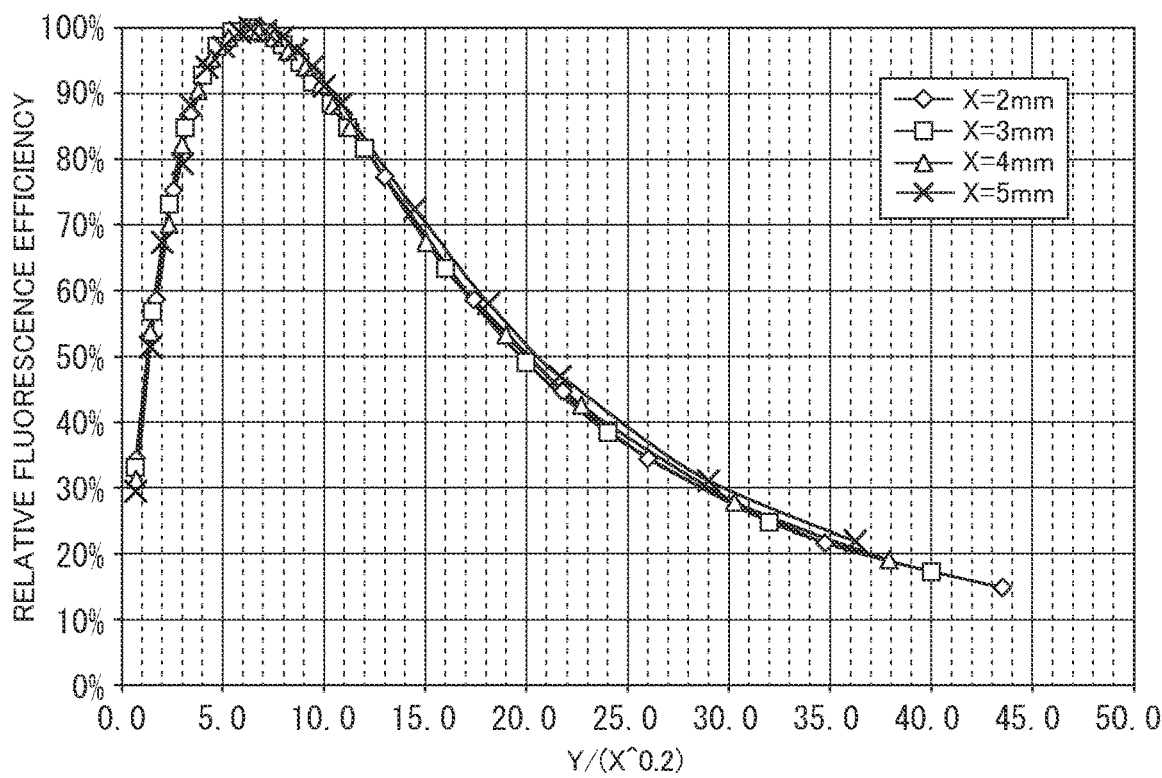
FIG. 5 is an example of a characteristic diagram illustrating a relationship between a function "Y/(X^0.2)", including the length X of, of the line through a light source and the first light receiving unit, the portion corresponding to the inside of the housing and a length Y of, of a line including a normal to a light receiving surface of a second light receiving unit, a portion corresponding to the inside of the housing, and the relative fluorescence efficiency.
Figure 6:
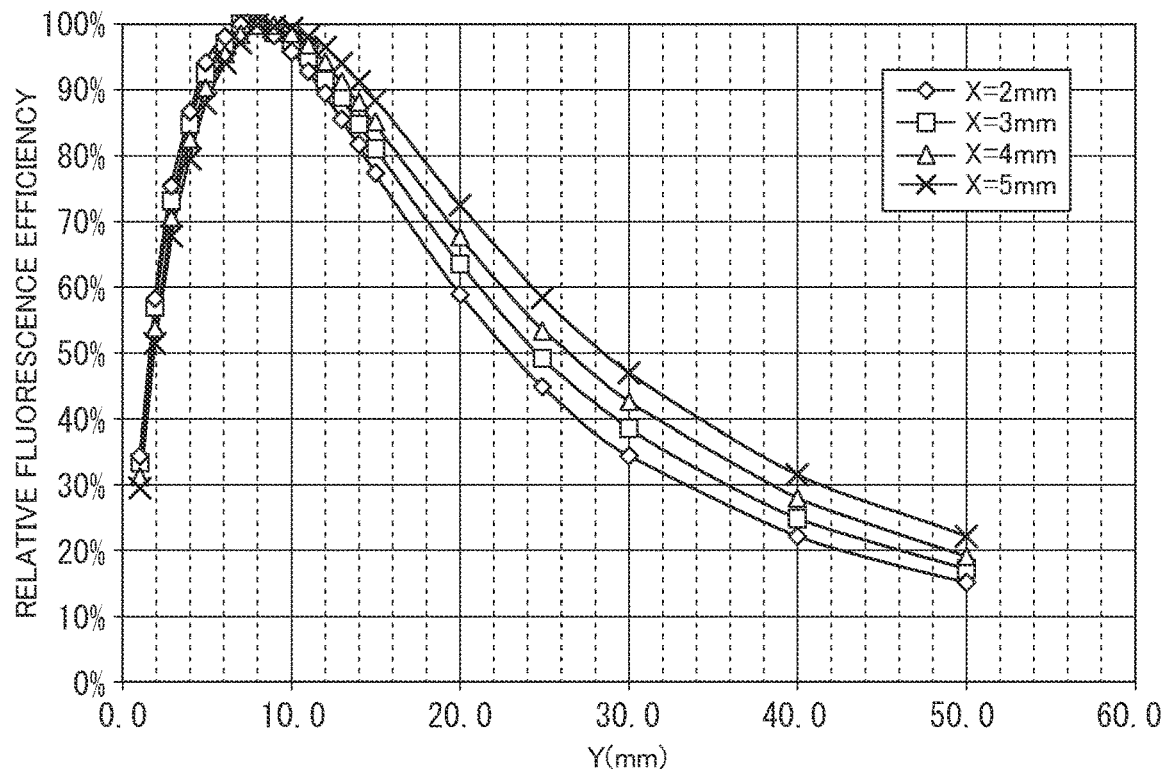
FIG. 6 is an example of a characteristic diagram illustrating a relationship between the length Y of, of the line including the normal to the light receiving surface of the second light receiving unit, the portion corresponding to the inside of the housing and the relative fluorescence efficiency.

Moreover, when a length of a portion of the line B present inside the housing is denoted by Y [mm] as illustrated in FIG. 2, from the perspective of relative fluorescence efficiency, a function "Y/(X^0.2) ("^" represents a power)", including the length Y and the length X of the line segment A1, is preferably $1.4 \leq Y/(X^{0.2}) \leq 20$ and $3.0 \leq Y/(X^{0.2}) \leq 13$ as illustrated in FIG. 5. If this range is set by only the length Y as illustrated in FIG. 6, it varies according to the value of the length X. By defining this by the function Y/(X^0.2) as illustrated in FIG. 5, a correlation between the length Y and the length X can be strictly set. If Y/(X^0.2) is within the above-described range, fluorescence having appropriate intensity in proportion to transmitted light can be measured, and a light path can be maintained in a straight line. Furthermore, the dynamic range of transmitted light which is often measured in a condition of high irradiation intensity and the dynamic range of fluorescence which is usually weak emission of light can be brought close to each other, and the concentrations of two constituents can be measured by using one light source without providing two light sources for them.

Moreover, in a case where the concentrations of two constituents can be measured by using one light source in this way, the shape of the housing is preferably a rectangular shape in a cross-sectional view of the housing along a plane including the light source and the first and second light receiving units. By configuring the housing to have a rectangular cross-section whose two parallel planes cross each other at right angles, the effect of stray light can be minimized as compared with a case where two parallel planes do not cross each other at right angles.

Furthermore, by setting the length X of the line segment A1 and the length Y of a portion of the line B present inside the housing to satisfy "Y/X>1", the effect of stray light can be further reduced. To prevent diffused reflection from the surface of the light source that is most likely to be a cause of stray light, Y/X preferably exceeds $2\sqrt{3}$. That is, a light source that irradiates light like diffused reflection from the surface can be generally considered as a light source that performs Lambertian radiation where the irradiance is proportional to the cosine of an angle between a normal to the plane and the incident angle of light. Therefore, if Y/X exceeds $2\sqrt{3}$, the angle between a normal to the plane of the light source and the position of the second light receiving unit can be increased, i.e., the cosine can be decreased. As a result, the irradiation intensity of stray light can be decreased to one-half or less, which corresponds to one bit in a digital circuit, and therefore can be decreased by one bit in a digital circuit. From the perspective of the maintenance of the linearity of the light path and the optimization of the distance between the light source and a sensor, Y/X is preferably less than 50, more preferably less than 20.

[Arithmetic Logical Unit]

The concentration measuring module according to the embodiment of the present invention may further include an arithmetic logical unit that calculates the concentration of each constituent contained in an irradiated body on the basis of outputs of the first and second light receiving units, i.e., first and second signals. Furthermore, the concentration measuring module may be provided with an amplifier circuit that amplifies an output of the second light receiving unit, and the arithmetic logical unit may perform an operation based on an output of the first light receiving unit and an output of the second light receiving unit that has been amplified by the amplifier circuit.

As an example of a specific method of calculating the concentration, there may be the following method; however, it is not particularly limited to this calculation method.

Since the absorbance of an irradiated body is proportional to the concentration Ca of a light-absorbing substance in the irradiated body, when the initial concentration of the light-absorbing substance in the irradiated body is denoted by Ca(0); an output of the first light receiving unit in a state where the irradiated body to be measured contains no light-absorbing substance is denoted by I(bl); and an output after time t is denoted by I(t), the concentration Ca(t) of the light-absorbing substance in the irradiated body after time t is calculated by the following equation (1). Incidentally, I(0) in equation (1) denotes an output of the first light receiving unit at the start of concentration measurement.

$$Ca(t)=Ca(0)\times(\log 10(I(t)/I(bl))/\log 10(I(0)/I(bl))) \quad (1)$$

By constantly recording Ca(t), the concentration of the light-absorbing substance in the irradiated body can be calculated in real time.

Furthermore, when an output of the second light receiving unit in a state where the irradiated body to be measured contains no fluorescent substance is denoted by Fb(bl); the initial concentration of a fluorescent substance in the irradiated body is denoted by Cb(0); and an output after time t is denoted by Fb(t), the concentration Cb(t) of the fluorescent substance in the irradiated body after time t is calculated by the following equation (2). Incidentally, Fb(0) in equation (2) denotes an output of the second light receiving unit at the start of concentration measurement.

$$Cb(t)=Cb(0)\times((Fb(t)-Fb(bl))/(Fb(0)-Fb(bl))) \quad (2)$$

By constantly recording Cb(t) and the value of integral of Cb(t), the concentration of the fluorescent substance in the irradiated body can be calculated in real time.

[Control Unit]

The concentration measuring module according to the embodiment of the present invention may further include a control unit that controls driving of the light source. The control unit has a function of driving the light source. As a specific example, the control unit may be a driver circuit using a MOS transistor as a drive transistor. As a specific condition for driving the light source, a constant current drive circuit driven by constant current may be used. Furthermore, the light source may be driven by direct drive current; however, from the perspective of power consumption, the light source may preferably be driven by pulses. To suppress radiation due to heat generated when the light source is driven, it may be more preferable to drive the light source by pulses. The specific duty ratio of the pulse drive is preferably 50% or less. To suppress the heat generation and the power consumption, the duty ratio may be 25%, or 10% or less, or even 5% or less.

Moreover, the control unit may drive the light source so that output light is emission pulses with a duty ratio of 20% or less. By using emission pulses with a duty ratio of 20% or less, concentration monitoring enabling to practically calculate the concentration as continuous data can be performed while suppressing the degradation of an LED due to heat and a decrease in luminous efficacy of the LED.

Specific Example of Embodiment

A specific example of an embodiment of the present invention is described below with reference to drawings; however, the embodiment described below is one aspect of the invention, and the invention is not limited to this.

Incidentally, components having the same configuration and function in the drawings are assigned the same reference numeral, and description of the same component is omitted.

FIG. 1 illustrates an example of a concentration measuring module 70 according to an embodiment of the present invention. The concentration measuring module 70 includes a housing 1, a light source 2, a first light receiving unit 3, a second light receiving unit 4, an irradiated body inlet 5, and an irradiated body outlet 6.

As illustrated in FIG. 1, the housing 1 has a shape of a hollow square tube having an almost square shape in a top view and a height shorter than the length of one side of the almost square. The irradiated body inlet 5 through which an irradiated body is introduced into the housing 1 is provided on one of a pair of facing side surfaces of the housing 1, and the irradiated body outlet 6 through which the irradiated body is discharged from the housing 1 is provided on the other side surface of the housing 1. Furthermore, the light source 2 is provided on the center of a top surface of the housing 1 in the top view, and the first light receiving unit 3 is provided in a position of an undersurface that faces the light source 2.

Moreover, the second light receiving unit 4 is provided on one of another pair of side surfaces different from the pair of facing side surfaces with the irradiated body inlet 5 and the irradiated body outlet 6 provided. The second light receiving unit 4 is provided roughly on the center of the side surface in a horizontal direction and a vertical direction.

In the concentration measuring module 70 illustrated in FIG. 1, an irradiated body flows into the housing 1 from the irradiated body inlet 5, and exits from the irradiated body outlet 6. Continuous flow into and out of an irradiated body continuously replaces the irradiated body in the housing 1, and changes in the concentration of the irradiated body in the housing 1 can be continuously monitored over time.

In this concentration measuring module 70, the light source 2 and the first light receiving unit 3 are arranged so that the light source 2 faces a light receiving surface of the first light receiving unit 3, and the housing 1 is arranged between them. Light emitted from the light source 2 linearly passes through the housing 1 and the irradiated body in the housing 1 and enters the first light receiving unit 3. Light energy is absorbed by the irradiated body during that time; therefore, the concentration of a light-absorbing constituent in the irradiated body is found by calculating the absorption by the irradiated body in accordance with the Lambert-Beer's law. To effectively use energy of the light source 2, the housing 1 is preferably less likely to absorb an emission wavelength of the light source 2, and, for example, quartz glass is used as a material of the housing 1.

Furthermore, in this concentration measuring module 70, the light source 2 and the second light receiving unit 4 are arranged so that a normal to a light emitting surface of the light source 2 is orthogonal to a normal to a light receiving surface of the second light receiving unit 4. The light emitted from the light source 2 excites a fluorescent substance in the irradiated body. The excited fluorescent substance isotropically glows; however, it radiates longer-wavelength light than the incident light from the light source 2, and therefore, the light radiated from the fluorescent substance is not absorbed by the fluorescent substance again. Since the emission intensity of the fluorescent substance is weaker than the incident light, the second light receiving unit 4 is arranged so as to maximize the view volume of a portion of the irradiated body irradiated by the light source 2. That is, the second light receiving unit 4 is arranged so that the normal to the light receiving surface of the second light receiving unit 4 forms a right angle with the normal to the light emitting surface of the light source 2.

Then, signals (first and second signals) detected in the first and second light receiving units 3 and 4 are input to an arithmetic logical unit 7. The arithmetic logical unit 7 receives the signals detected in the first and second light receiving units 3 and 4, and calculates the concentration of each constituent contained in the irradiated body on the basis of these detected signals. Furthermore, the light source 2 is driven by a control unit 8 by an appropriate method, for example, pulse drive, continuous lighting, or intermittent drive.

FIG. 2 is a cross-sectional view illustrating an example of the arrangement of the light source 2, the first light receiving unit 3, and the second light receiving unit 4 included in the concentration measuring module 70 according to the embodiment of the present invention.

The length X in FIG. 2, i.e., a length of, of a line connecting the light source 2 with the first light receiving unit 3, a portion corresponding to the inside of the housing 1 is determined according to the absorbance of the irradiated body that is an object of concentration measurement with respect to an emission wavelength of the light source 2. The concentration of a light-absorbing constituent in the irradiated body varies during the monitoring; however, when an absorption coefficient at the highest concentration of a target light-absorbing constituent in the irradiated body is denoted by Emax/cm, and an absorption coefficient at the lowest concentration is denoted by Emin/cm, $10^{(-Emin \times X)}$ is the maximum value of transmittance, and $10^{(-Emax \times X)}$ is the minimum value of transmittance. The length X is set so as to maximize Idef expressed in equation (3). Incidentally, X in equation (3) is a length of, of the line segment A connecting the light source 2 with the first light receiving unit 3 illustrated in FIG. 2, a portion corresponding to the inside of the housing 1. Furthermore, "^" represents a power, and Idef is an index of the dynamic range of a target solution to be measured.

$$Idef = 10^{(-Emin \times X)} - 10^{(-Emax \times X)} \qquad (3)$$

By doing this, the S/N ratio can be improved within a necessary concentration range. Uric acid can be used as a substance for monitoring a urea-like substance contained in spent dialysate; however, its concentration varies according to a dialysis condition. Uric acid in spent dialysate is generally 0.5 mg/dL or more, and 4.0 mg/dL or less on average, and even in consideration of the variation due to a dialysis condition, if uric acid is 8.0 mg/dL or less, it is applicable, and its concentration measurement can be performed. Actually, we checked an absorption coefficient of uric acid in a solution when an emission wavelength of the light source 2 was 280 nm, it was 0.50/cm·(mg/dL).

As a result of consideration based on the assumption that, in the concentration measuring module 70 according to the embodiment of the present invention illustrated in FIG. 1, an LED having an emission wavelength of 280 nm is used as the light source 2, and the concentration of uric acid in spent dialysate is monitored as a urea-like substance, we came to a conclusion that a preferred length X is 2 mm or more and 5 mm or less, including the length at which Idef reaches a peak as illustrated in FIG. 3.

Incidentally, in FIG. 3, the horizontal axis represents the length X of the line segment A1 that is a portion belonging to the inside of the housing of the line segment A connecting the light source 2 with the first light receiving unit 3; and the vertical axis represents Idef. As illustrated in FIG. 3, Idef reaches a peak when X is 3 mm; Idef decreases with increase of X from 3 mm, and decreases with decrease of X from 3 mm.

Figure 4:
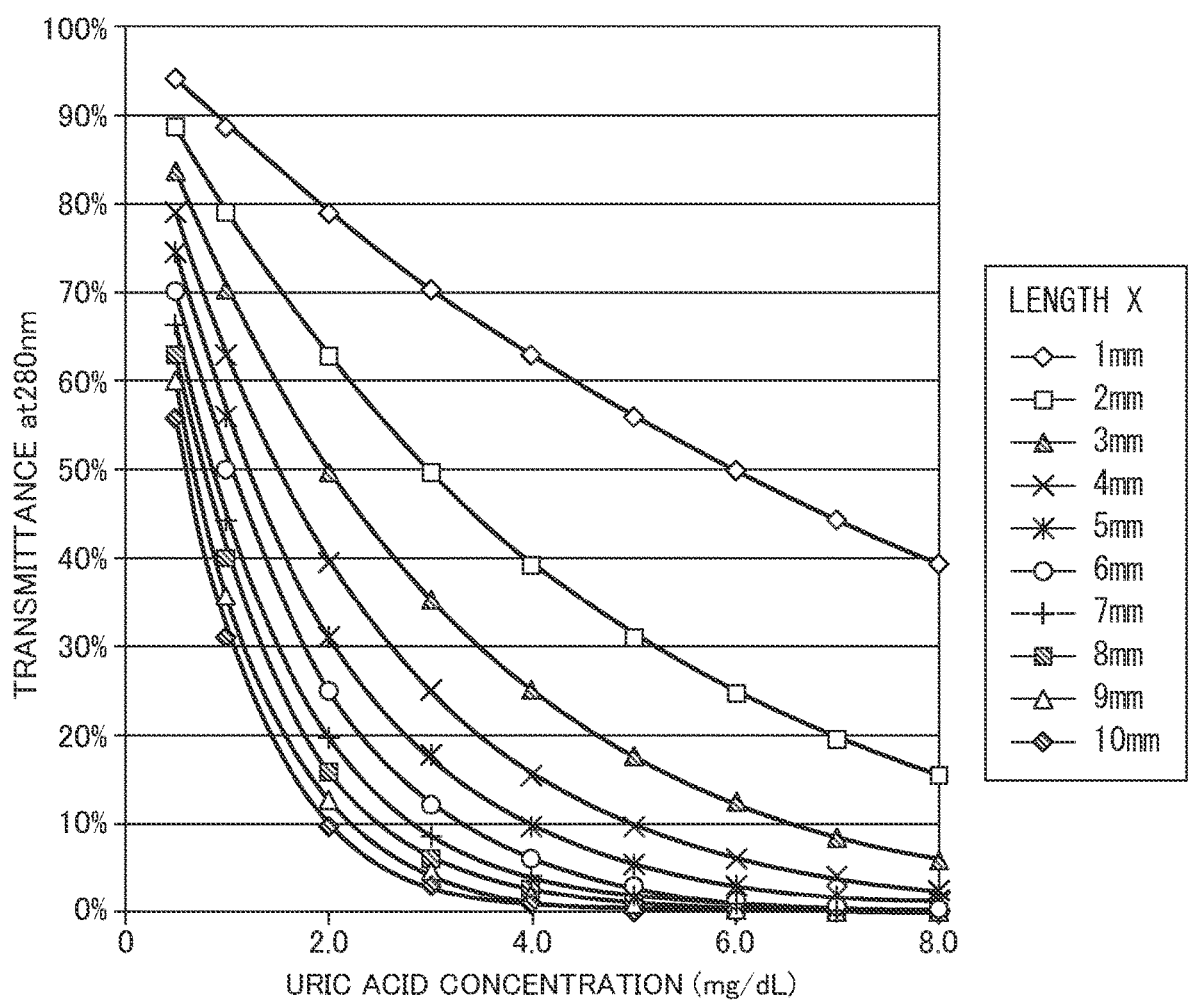
FIG. 4 is an example of a characteristic diagram illustrating a relationship between the uric acid concentration (mg/dL) with respect to, of the line through the light source and the first light receiving unit, each portion corresponding to the inside of the housing and the transmittance when a wavelength of the light source is 280 nm.

Furthermore, as illustrated in FIG. 4, in a case where Idef is in the same range, a shorter length X causes better linearity in a relationship between the uric acid concentration and the transmittance. Incidentally, in FIG. 4, the horizontal axis represents the uric acid concentration (mg/dL), and the vertical axis represents the transmittance when the wavelength of the light source 2 is 280 nm. Furthermore, characteristic lines in FIG. 4 differ in the length X; the smaller the value of transmittance with respect to the uric acid concentration in FIG. 4, the larger the value of X a characteristic line has.

Which one of Idef and the linearity in the relationship between the uric acid concentration and the transmittance is given priority depends on the amplification performance of the light receiving unit; however, if Idef exceeds "0.7", a condition for better linearity may be given priority.

On the other hand, as described above, the length Y in FIG. 2 is set to increase with expansion of emission of the light source 2 because the larger view volume of the first light receiving unit 3 is preferable. A window portion made of a material that allows output light of the light source 2 to pass therethrough is formed on a portion of the housing 1 that faces the light receiving surface of the first light receiving unit 3; in a case where the circular light receiving surface of the first light receiving unit 3 is provided on this window portion, the length Y is set to be larger than the diameter of the circular window portion provided for the first light receiving unit 3. The upper limit of the length Y is limited by the absorbance of a wavelength of fluorescence of the irradiated body; however, it is preferably smaller than 20 times the value of the diameter of an opening of the circular window portion because the distance from the light source may become too long when the second light receiving unit is arranged.

FIG. 5 illustrates a correlation between the length X of the line segment A1, the length Y of the portion of the line B present inside the housing and relative fluorescence efficiency. In FIG. 5, the horizontal axis represents the function "Y/(X^0.2)" including X and Y, and the vertical axis represents relative fluorescence efficiency; FIG. 5 is an example of a characteristic diagram in which the intensity of fluorescence generated when the uric acid concentration is 8 mg/dL is relatively displayed as a maximum value of 100%. Furthermore, FIG. 6 is a characteristic diagram representing the characteristic diagram in FIG. 5 with Y as the horizontal axis, where the horizontal axis represents Y, and the vertical axis represents relative fluorescence efficiency. FIG. 6 is an example of a characteristic diagram in which the intensity of fluorescence generated when the uric acid concentration is 8 mg/dL is relatively displayed as a maximum value of 100%. The characteristic diagrams in FIGS. 5 and 6 both illustrate cases of the length X of 2 mm, 3 mm, 4 mm, and 5 mm.

It can be seen from FIG. 5 that when the function "Y/(X^0.2)" is 1.4≤Y/(X^0.2)≤20, relative fluorescence efficiency is 50% or more; and when the function "Y/(X^0.2)" is 3.0≤Y/(X^0.2)≤13, relative fluorescence efficiency is 70% or more. By setting the length X of the line segment A1 and the length Y of the portion of the line B present inside the housing so that the function "Y/(X^0.2)" satisfies 1.4≤Y/(X^0.2)≤20, more preferably 3.0≤Y/(X^0.2)≤13, sufficient relative fluorescence efficiency can be obtained, and fluorescence having appropriate intensity in proportion to transmitted light can be measured. Furthermore, the dynamic range of transmitted light which is often measured in a condition of high irradiation intensity and the dynamic range of fluorescence which is usually weak emission of light can be brought close to each other, and the concentrations of two different substances can be measured by using one light source.

Figure 7:
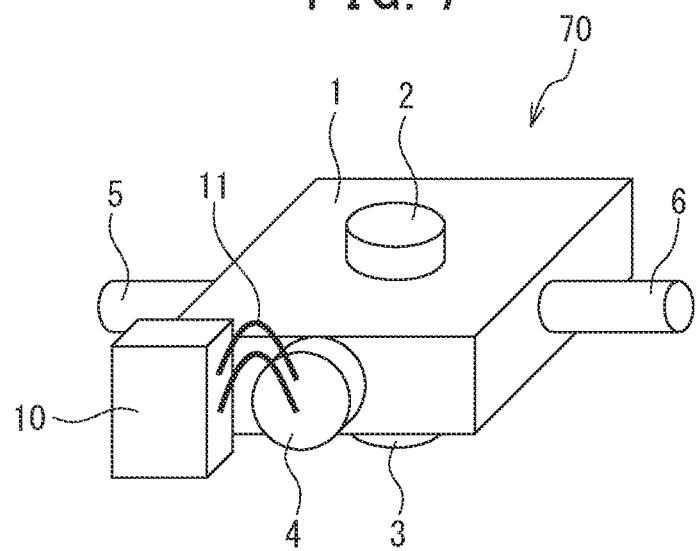
FIG. 7 is a conceptual diagram illustrating an example of a configuration of a concentration measuring module including an amplifier circuit.

FIG. 7 illustrates an example of a schematic configuration of the concentration measuring module 70 including an amplifier circuit 10. The amplifier circuit 10 is connected to a photoreceptor of the second light receiving unit 4 by a wiring 11, and an output of the amplifier circuit 10 is input to the arithmetic logical unit 7. At this time, the inter-circuit straight-line distance, i.e., the distance in a straight line between the center of a photoreceptor of the second light receiving unit 4 and a point at which the wiring 11 is in contact with the amplifier circuit 10 is 5 cm or less, more preferably 2 cm or less.

Figure 8:
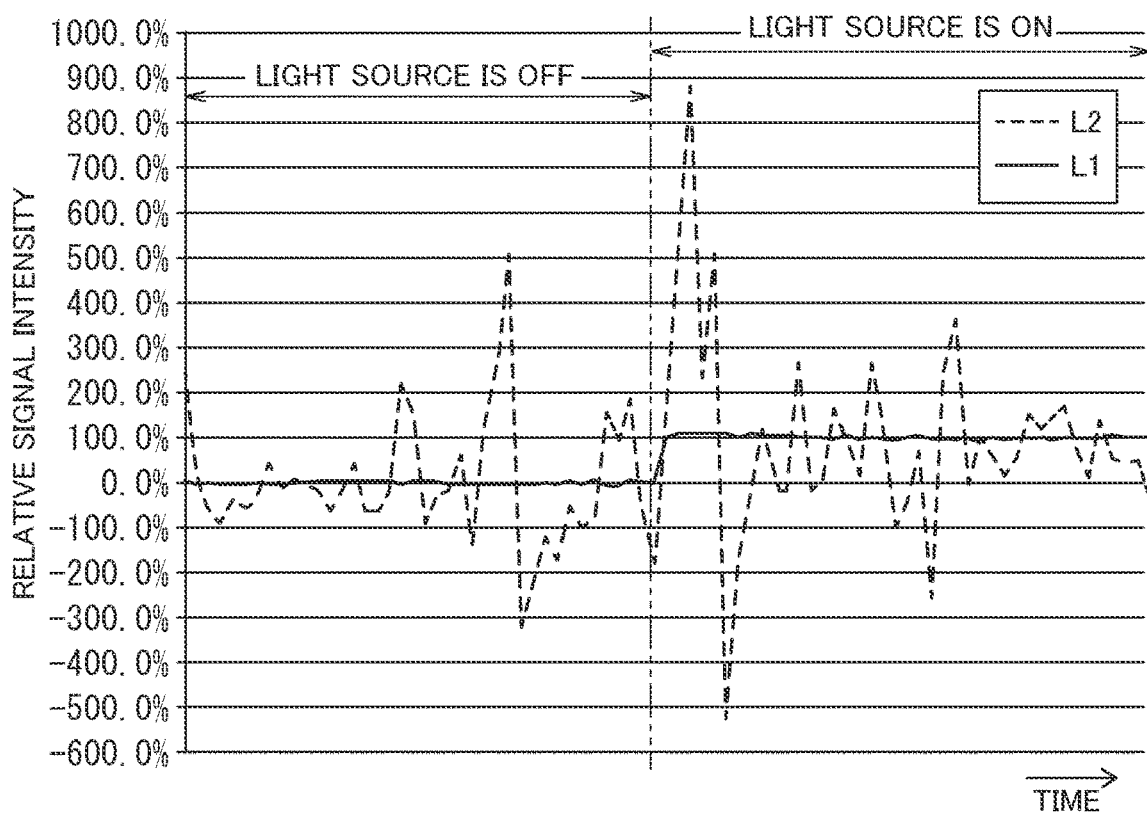
FIG. 8 is a characteristic diagram illustrating an example of the relative signal intensity obtained from the second light receiving unit.

FIG. 8 plots the relative signal intensity with time to compare noise in a case where the inter-circuit straight-line distance is 2 cm and noise in a case where the inter-circuit straight-line distance is 40 cm; the relative signal intensity is based on two average values: an average value of second signals obtained from the second light receiving unit 4 when the light source 2 is in off-state as 0%, and an average value of second signals obtained from the second light receiving unit 4 when the light source 2 is in on-state as 100%.

In FIG. 8, the horizontal axis represents time, and the vertical axis represents the relative signal intensity. Furthermore, a characteristic line L1 indicates the relative signal intensity with time in the case where the inter-circuit straight-line distance is 2 cm; a deviation from 0% indicates the magnitude of noise in a section in which the light source 2 is off, and a deviation from 100% indicates the magnitude of noise in a section in which the light source 2 is on. A characteristic line L2 indicates the relative signal intensity with time in the case where the inter-circuit straight-line distance is 40 cm; a deviation from 0% indicates the magnitude of noise in a section in which the light source 2 is off, and a deviation from 100% indicates the magnitude of noise in a section in which the light source 2 is on.

As illustrated in FIG. 8, it can be seen that noise is significantly reduced in the case of an inter-circuit straight-line distance of 2 cm indicated by the characteristic line L1 as compared with the case of an inter-circuit straight-line distance of 40 cm.

Figure 9:
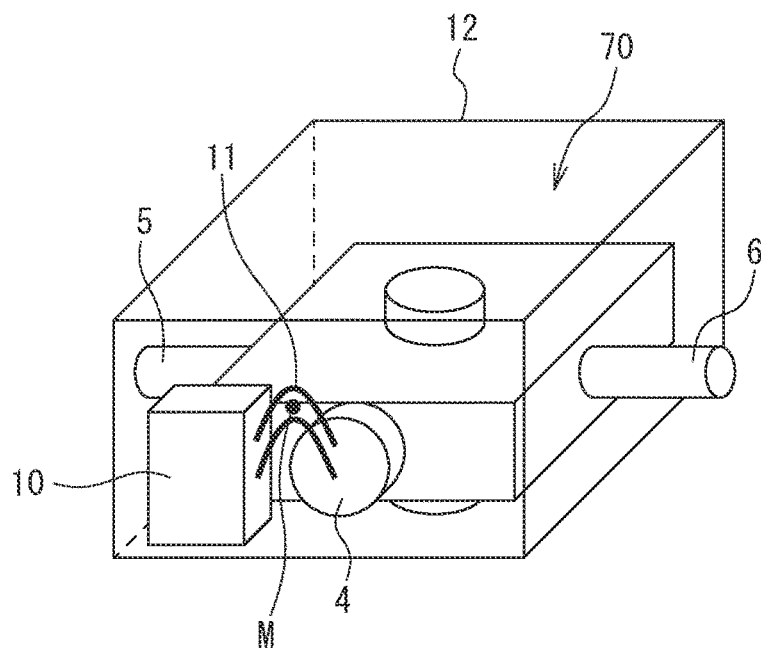
FIG. 9 is a conceptual diagram illustrating a configuration example of a case where the concentration measuring module and the amplifier circuit are shielded.

FIG. 9 illustrates an example of a case where the concentration measuring module 70 and the amplifier circuit 10 of the second light receiving unit 4 are covered with a good conductor. In FIG. 9, the concentration measuring module 70 and the amplifier circuit 10 of the second light receiving unit 4 are covered with a good conductor in such a manner that the concentration measuring module 70 and the entire amplifier circuit 10 of the second light receiving unit 4 are housed in a housing 12 formed of a good conductor of electricity, such as aluminum or copper, and the irradiated body inlet 5 and the irradiated body outlet 6 are pulled out of the housing 12 through holes 12a and 12b formed on the housing 12.

Figure 10:
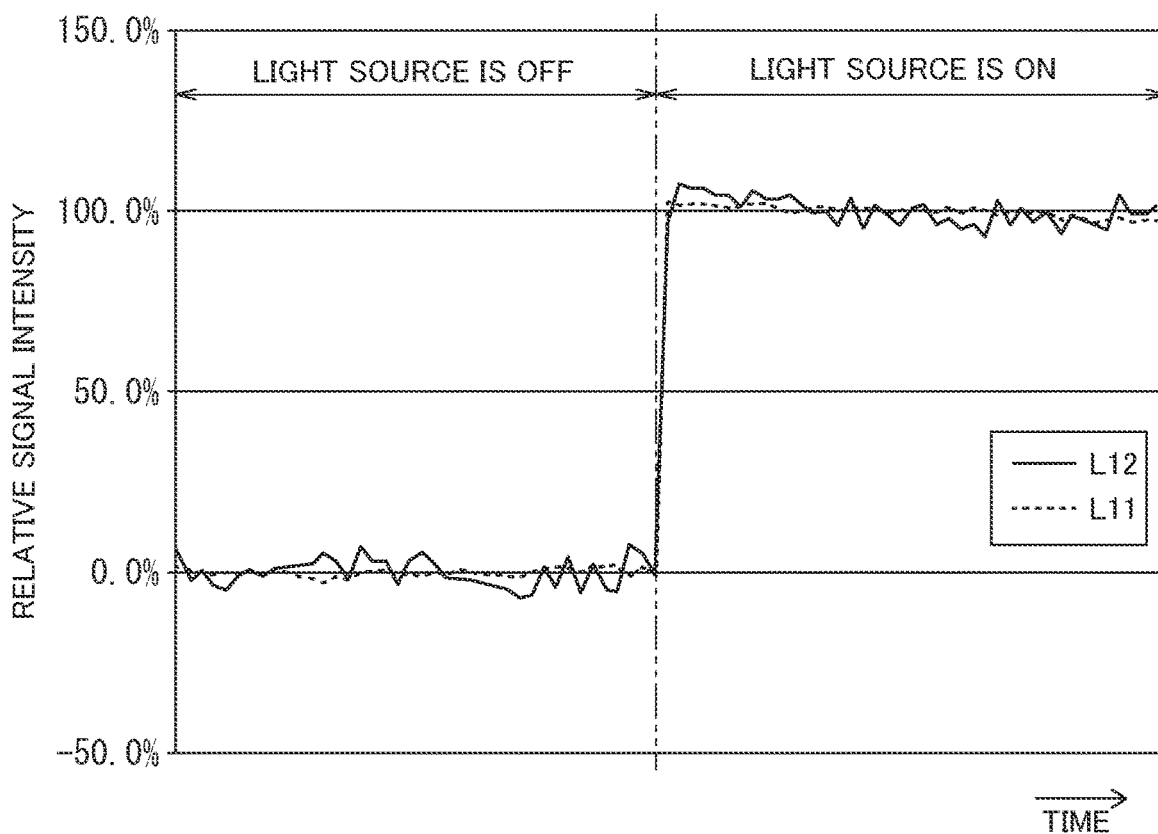
FIG. 10 is a characteristic diagram illustrating an example of the relative signal intensity obtained from the second light receiving unit.

FIG. 10 plots the relative signal intensity with time to compare noise in a case where the concentration measuring module 70 and the amplifier circuit 10 of the second light receiving unit 4 are covered with a good conductor, i.e., are electrically shielded and noise in a case where they are not electrically shielded; the relative signal intensity is based on two average values: an average value of second signals obtained from the second light receiving unit 4 when the light source 2 is in off-state as 0%, and an average value of second signals obtained from the second light receiving unit 4 when the light source 2 is in on-state as 100%.

In FIG. 10, the horizontal axis represents time, and the vertical axis represents the relative signal intensity. Furthermore, a characteristic line L11 indicates the relative signal intensity with time in the case where the concentration measuring module 70 and the amplifier circuit 10 of the second light receiving unit 4 are electrically shielded; a deviation from 0% indicates the magnitude of noise in a section in which the light source 2 is off, and a deviation from 100% indicates the magnitude of noise in a section in which the light source 2 is on. A characteristic line L12 indicates the relative signal intensity with time in the case where the concentration measuring module 70 and the amplifier circuit 10 of the second light receiving unit 4 are not electrically shielded; a deviation from 0% indicates the magnitude of noise in a section in which the light source 2 is off, and a deviation from 100% indicates the magnitude of noise in a section in which the light source 2 is on.

As illustrated in FIG. 10, it can be seen that noise is reduced in the case indicated by the characteristic line L11 where the concentration measuring module 70 and the amplifier circuit 10 of the second light receiving unit 4 are electrically shielded as compared with the case where they are not electrically shielded.

Incidentally, in the above-described embodiment, the concentration measuring module 70 are configured to be provided with two light receiving units: the first light receiving unit 3 and the second light receiving unit 4 and detect the concentrations of two constituents contained in an irradiated body; however, it is not limited to this configuration. For example, a third light receiving unit having sensitivity to excitation light of a third wavelength different from the second light receiving unit 4 may be provided on a surface facing the side surface with the second light receiving unit 4 provided, and the third light receiving unit may receive excitation light excited by output light of the light source 2, and the concentration of a constituent included in the irradiated body that radiates excitation light of the third wavelength may be measured on the basis of an output signal from the third light receiving unit. The concentrations of four or more constituents included in the irradiated body may be measured simultaneously by the same procedure.

Subsequently, a case where the above-described concentration measuring module 70 is applied to the measurement of concentrations of wastes in spent hemodialysate is described as another example of an embodiment of the present invention.

Figure 11:
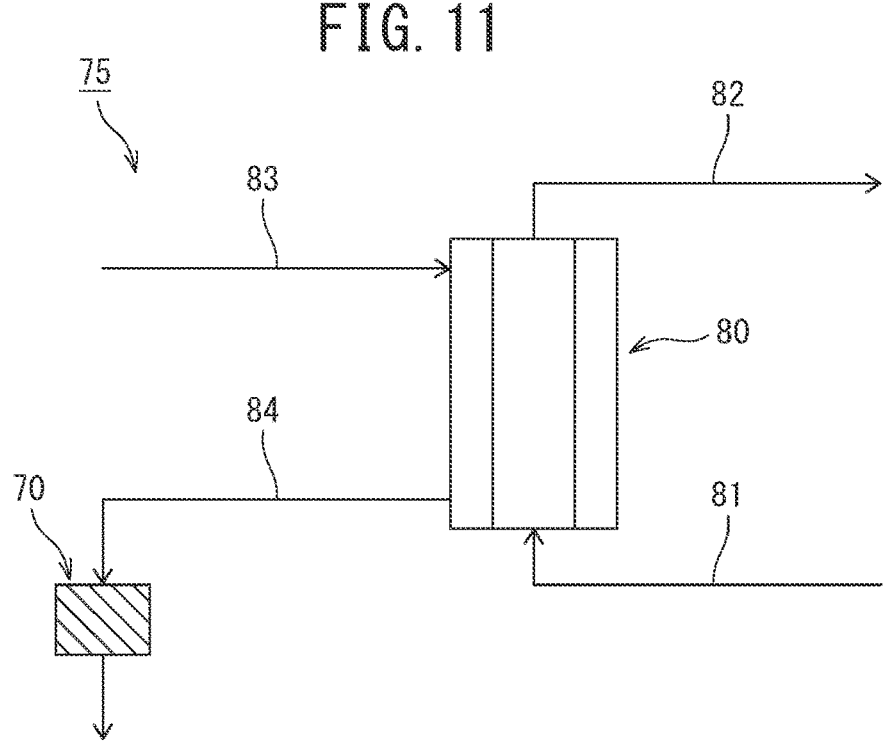
FIG. 11 is a conceptual diagram illustrating a configuration example of a dialyzer according to another embodiment of the present invention.

FIG. 11 is a conceptual diagram illustrating a configuration example of a hemodialyzer 75 according to a first embodiment of the present invention.

As illustrated in FIG. 11, this hemodialyzer 75 is equipment having a wastes configuration measuring function using ultraviolet light absorption of spent dialysate. The hemodialyzer 75 includes a dialyzer 80 that is a blood purifier with a hollow fiber membrane including a polymer porous membrane; a line 81 connected to an arterial-side blood circuit of a blood circuit connected to the dialyzer 80; a line 82 connected to a venous-side blood circuit of the blood circuit connected to the dialyzer 80; a dialysate introduction line 83 that is one of dialysate lines connected to the dialyzer 80; a dialysate discharge line 84 that is one of the dialysate lines connected to the dialyzer 80; and the concentration measuring module 70 connected to the dialysate discharge line 84.

The dialyzer 80 includes a plurality of hollow fibers, the inside of the hollow fibers and the outside of the hollow fibers form different channels, liquid contained in the inside of the hollow fibers and the outside of the hollow fibers is separated across a hollow fibers polymer membrane. In general, the inside of the hollow fibers is connected to the lines 81 and 82 connected to the arterial-side blood circuit and the venous-side blood circuit, respectively, and the outside of the hollow fibers is connected to the dialysate introduction line 83 and the dialysate discharge line 84. Wastes in the blood go through the hollow fibers, and diffuse to the side of dialysate, and then are discharged into the dialysate discharge line 84. When the wastes in the spent dialysate pass through the concentration measuring module 70, the transmittance and the intensity of fluorescence are measured.

In dialysis treatment, generally, a blood test is performed earlier that week before the start of the dialysis, and the serum urea nitrogen concentration is measured. When this concentration is denoted by $C1(0)$, since the absorbance when an emission wavelength of the light source 2 is about 280 nm is proportional to $C1(0)$, the blood urea nitrogen concentration $C1(t)$ after a lapse of time t since the start of circulation of the blood is calculated by the following equation (4), where Ibl denotes an output of the first light receiving unit 3 when the concentration measuring module 70 performs concentration measurement in a state where the dialysate introduction line 83 and the dialysate discharge line 84 are filled with only dialysate before the circulation of the blood (before the blood to be measured is circulated); I(0) denotes an output of the first light receiving unit 3 just after the start of the circulation of the blood (just after the circulation of the blood to be measured has started); and I(t) denotes an output of the first light receiving unit 3 after the lapse of time t since the start of circulation of the blood.

$$C1(t)=C1(0)\times(\log 10(I(t)/Ibl)/\log 10(I(0)/Ibl)) \quad (4)$$

By constantly recording $C1(t)$, a dialysis dose Kt/V can be calculated in real time. Incidentally, K denotes clearance of a substance that is an object to the dialysis; t denotes a time; V denotes a body fluid volume. Therefore, the dialysis can be continued until the end of the dialysis decided by doctor's judgment, i.e., a point at which Kt/V has become 1.2 or more and 1.8 or less, and can end exactly at that point. Accordingly, it becomes possible to ease a strain on a dialysis patient caused by excessive dialysis.

Furthermore, the blood albumin concentration $C2(t)$ after a lapse of time t since the start of circulation of the blood is calculated by the following equation (5), where Fbl denotes an output of the second light receiving unit 4 in a state where the dialysate introduction line 83 and the dialysate discharge line 84 are filled with only dialysate before the circulation of the blood to be measured; F(0) denotes an output of the second light receiving unit 4 just after the start of the circulation of the blood; and F(t) denotes an output of the second light receiving unit 4 after the lapse of time t since the start of circulation of the blood.

$$C2(t)=C2(0)\times((F(t)-Fbl)/(F(0)-Fbl)) \quad (5)$$

By constantly recording $C2(t)$ obtained by equation (5) and the value of integral of $C2(t)$, an amount of albumin leakage during dialysis can be calculated in real time, which makes it possible to grasp the amount of albumin leakage without waiting for a blood test, and also possible to change the condition for necessary dialysis according to doctor's judgment. Accordingly, it is possible to perform dialysis while keeping the amount of albumin leakage to less than a predetermined amount and increasing a removal amount of β2-microglobulin.

EXAMPLE

An example of the concentration measuring module 70 according to the embodiment of the present invention is more specifically described below; however, the invention is not limited to this.

A case where the above-described concentration measuring module 70 is applied to the simultaneous measurement of the urea-like substance concentration and the aluminum concentration is described as an example of an embodiment of the present invention.

Uric acid was used as a urea-like substance. Uric acid can be used as a substance for monitoring a urea-like substance in spent dialysate. By reference to the change in uric acid concentration in spent dialysate under a general dialysis condition, a test solution was adjusted at a concentration of 0.5 mg/dL and 8.0 mg/dL or less.

Bovine serum-derived albumin was used as albumin. Although an amount of albumin leakage varies according to the membrane performance and the dialysis condition, an amount of albumin leakage per dialysis is about 10 g at a maximum. In dialysis using a dialyzer having low membrane performance, the amount of leakage may sometimes be a small amount below 1 g; however, in such a membrane-performance dialyzer, the amount of albumin leakage is never a problem. Based on a dialysis condition of a general high-performance dialyzer called IV-type or V-type dialyzer, we determined that it would be of clinical value if it can measure an albumin concentration of 0.5 mg/dL or more and 20.0 mg/dL or less.

Uric acid as a solute and albumin were dissolved in a boric-acid buffer solution with a pH of 9.18, and this solution was used in the measurement.

As a housing, an ultraviolet-light-transmissive housing that is made of quartz glass and has a length X of 2 mm and a length Y of 10 mm was used in the measurement.

As a light source, a deep ultraviolet LED having a peak emission wavelength of 280 nm was used. Furthermore, the light source was driven by emission of pulses with a duty ratio of 20% every second.

As a first light receiving unit, a SiC photodiode having sensitivity to the emission wavelength of the deep ultraviolet LED was used. As a second light receiving unit, a Si photodiode having sensitivity to 340-nm peak fluorescence of albumin was used.

Figure 12:
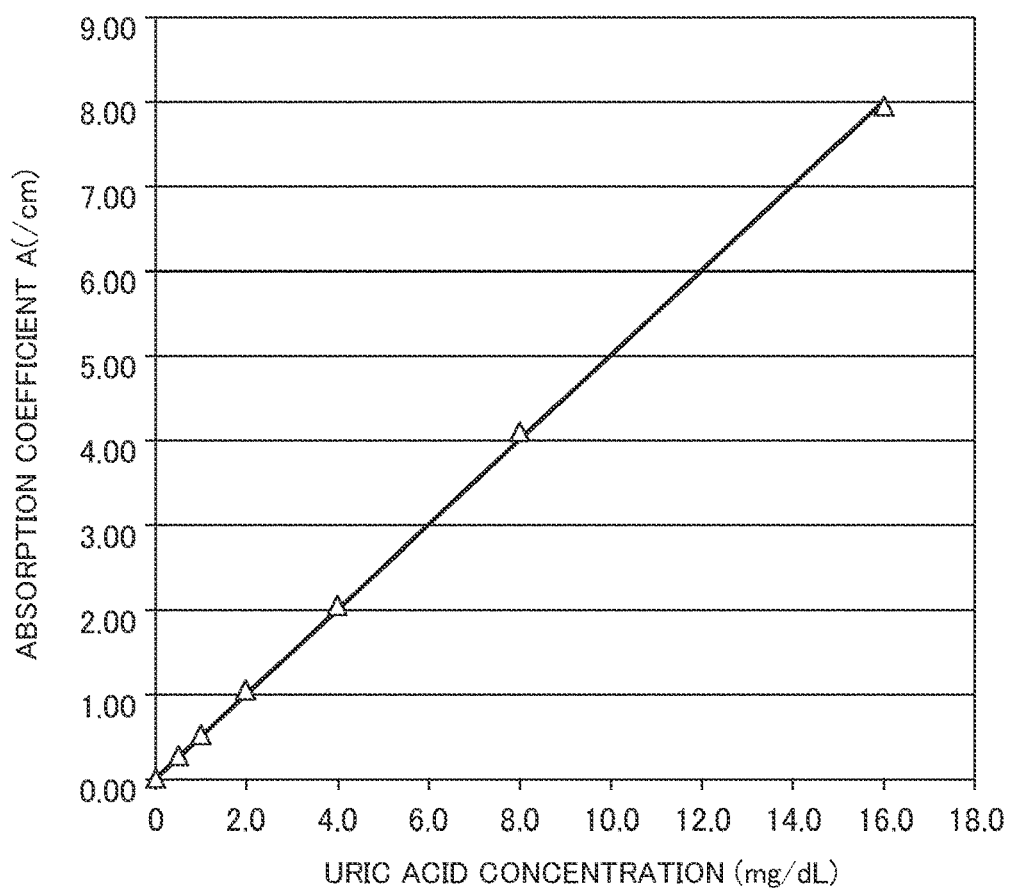
FIG. 12 is an example of a characteristic diagram illustrating correspondence between the uric acid concentration and an absorption coefficient.

FIG. 12 is a graph illustrating an example of the uric acid concentration in a uric-acid boric-acid buffer solution containing no albumin and the absorption coefficient calculated from a first signal output from the first light receiving unit 3 of the concentration measuring module 70.

It can be seen that the first signal according to the Lambert-Beer's law with respect to the uric acid concentration was obtained. Incidentally, in FIG. 12, the horizontal axis represents the uric acid concentration (mg/dL), and the vertical axis represents the absorption coefficient A (/cm).

Figure 13:
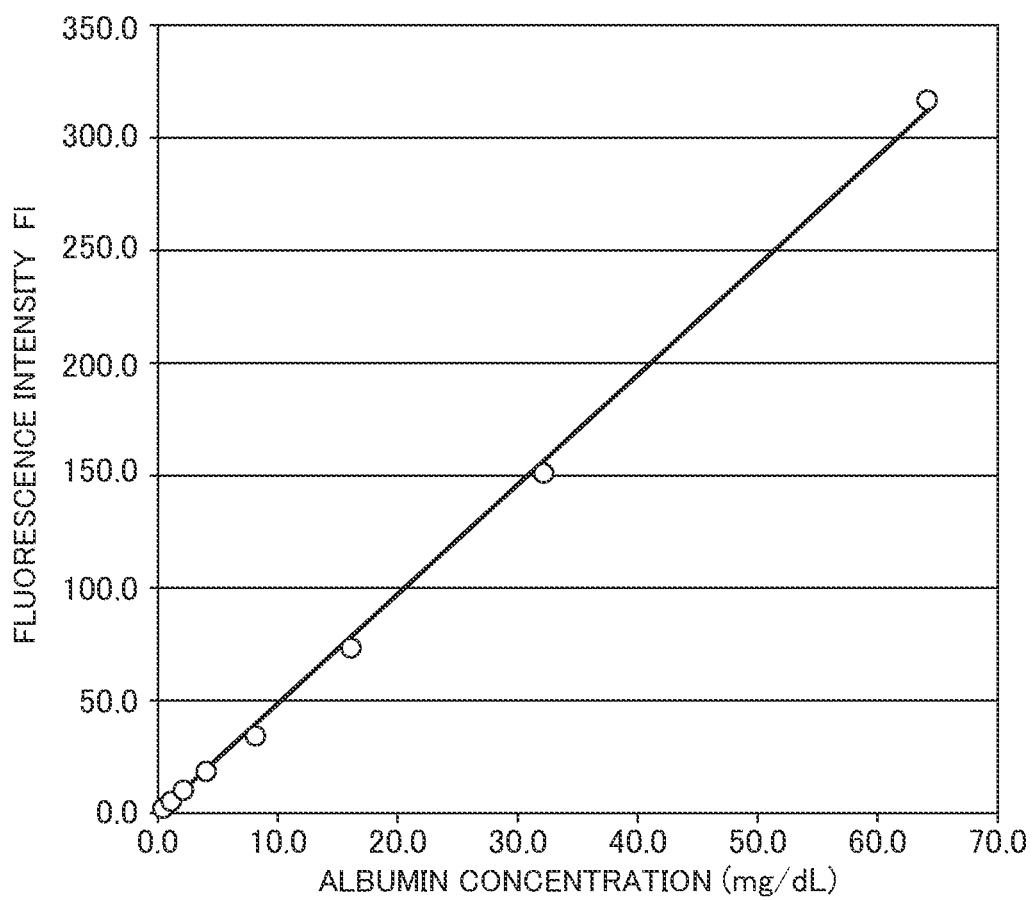
FIG. 13 is an example of a characteristic diagram representing correspondence between the albumin concentration and the fluorescence intensity.

FIG. 13 is a graph illustrating an example of the albumin concentration in an albumin boric-acid buffer solution containing no uric acid and the fluorescence intensity Fl obtained from a second signal output from the second light receiving unit 4 of the concentration measuring module 70.

It can be seen that the second signal depending on fluorescence according to the albumin concentration was obtained. In FIG. 13, the horizontal axis represents the albumin concentration (mg/dL), and the vertical axis represents the fluorescence intensity Fl. The fluorescence intensity Fl is a digital value into which an amplified analog value of an electrical signal (a second signal) obtained from the second light receiving unit 4 is converted, and the unit is an arbitrary unit (a.u.).

FIG. 14 is an example of first and second signals obtained from the first and second light receiving units when boric-acid buffer solutions with albumin concentrations of 8.0 mg/dL, 16.0 mg/dL, 32.0 mg/dL were used when the uric acid concentrations were 0.0 mg/dL, 1.0 mg/dL, 2.0 mg/dL, 4.0 mg/dL, and 8.0 mg/dL. Incidentally, in FIG. 14, the absorption coefficient is illustrated as a first signal obtained from the first light receiving unit, and the fluorescence intensity Fl is illustrated as a second signal obtained from the second light receiving unit.

Since excitation light is decreased by absorption of a solution, there becomes no correlation between the actual albumin concentration and the fluorescence intensity; however, by calculating Fl_norm using transmittance T1 measured by the first light receiving unit 3 in the present invention and correction based on equation (6), a correlation having good linearity can be obtained.

Corrected fluorescence intensity
$$Fl\_norm = \text{Fluorescence intensity } Fl \div (0.797 \times T1 + 0.203) \quad (6)$$

Incidentally, "0.797" in equation (6) is slope of a correction function found from the transmittance and the fluorescence intensity, and "0.203" is an intercept of the correction function found from the transmittance and the fluorescence intensity. The correction function is a linear function to approximate solutions with the same albumin concentration and different uric acid concentrations in uric-acid boric-acid buffer solutions by the least-squares method with the transmittance as the horizontal axis and the fluorescence intensity as the vertical axis, a coefficient of the correction function is used by normalizing to a value obtained by setting the fluorescence when the transmittance is 100% as 1.0.

Figure 15:
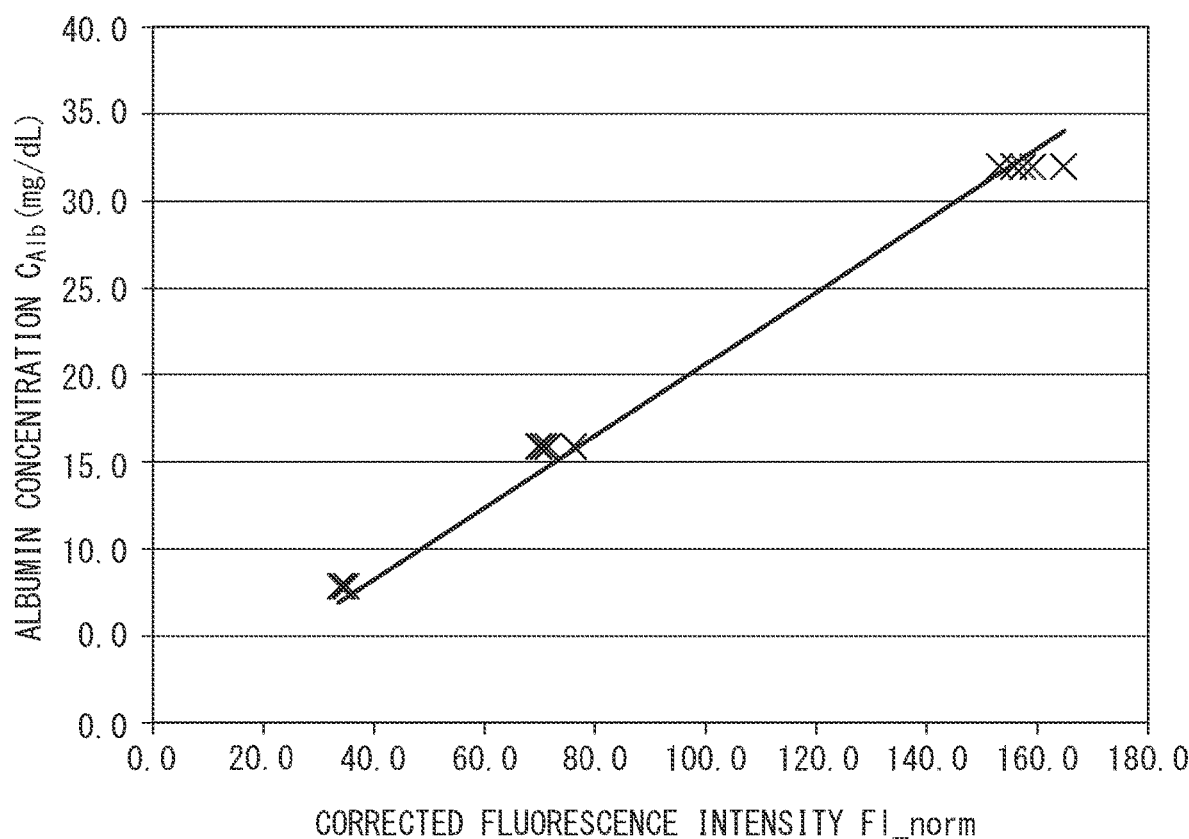
FIG. 15 is a characteristic diagram illustrating a linear relationship represented by the corrected fluorescence intensity Fl_norm.

FIG. 15 illustrates a linear relationship represented by the corrected fluorescence intensity Fl_norm. It can be seen that even in a situation that uric acid and albumin coexisted, the albumin concentration could be appropriately detected. Incidentally, in FIG. 15, the horizontal axis represents the corrected fluorescence intensity Fl_norm, and the vertical axis represents the albumin concentration $C_{Alb}$ (mg/dL).

The above results confirmed that the concentration measuring module 70 according to the present invention can measure the concentrations uric acid and albumin coexisting in spent dialysate with accuracy enough for practical use.

DESCRIPTION OF REFERENCE NUMERALS 1 housing
2 light source
3 first light receiving unit
4 second light receiving unit
5 irradiated body inlet
6 irradiated body outlet
70 concentration measuring module
75 hemodialyzer
80 dialyzer
81 line connected to arterial-side blood circuit
82 line connected to venous-side blood circuit
83 dialysate introduction line
84 dialysate discharge line

What is claimed is:
1. A concentration measuring module comprising:
a housing configured to be able to house an irradiated body;

a light source configured to emit light into the housing;

a first light receiving unit configured to have sensitivity to a wavelength of output light of the light source and receive light radiated from inside the housing; and a second light receiving unit configured to have sensitivity to a longer wavelength than the first light receiving unit and receive light radiated from inside the housing, wherein the light source and the first light receiving unit are arranged so that a light emitting surface of the light source faces a light receiving surface of the first light receiving unit, the light source, the first light receiving unit, and the second light receiving unit are arranged to have a positional relationship in which a normal to a light receiving surface of the second light receiving unit is orthogonal to a line segment corresponding to the inside of the housing, of a line through the light source and the first light receiving unit, a length X of the line segment corresponding to the inside of the housing, of the line through the light source and the first light receiving unit, and a length Y of a line segment corresponding to the inside of the housing, of a line including the normal to the light receiving surface of the second light receiving unit, satisfy $3.0 \le Y/(X^{0.2}) \le 13$, and the length X of the line segment and the length Y of the line segment satisfy $2\sqrt{3} < Y/X < 50$.

2. The concentration measuring module according to claim 1, wherein the first light receiving unit receives light having been transmitted through the inside of the housing of the output light and has sensitivity to a wavelength of light attenuated by the irradiated body, of the output light, and the second light receiving unit receives excitation light inside of the housing excited by the output light of the light source and has sensitivity to excitation light that the irradiated body excited by the output light radiates and has a longer wavelength than the output light.

3. The concentration measuring module according to claim 1, wherein the irradiated body contains two or more constituents.

4. The concentration measuring module according to claim 1, wherein a view volume P of the first light receiving unit with respect to the inside of the housing and a view volume Q of the second light receiving unit with respect to the inside of the housing satisfy $1 \le Q/P \le 200$.

5. The concentration measuring module according to claim 1, wherein the normal to the light receiving surface of the second light receiving unit passes through a midpoint of, of the line through the light source and the first light receiving unit, the line segment corresponding to the inside of the housing.

6. The concentration measuring module according to claim 1, wherein the length X of the line segment satisfies $1\ mm \le X \le 10\ mm$.

7. The concentration measuring module according to claim 1, wherein the length X of the line segment satisfies $2\ mm \le X \le 5\ mm$.

8. The concentration measuring module according to claim 1, wherein a shape of the housing is a rectangular shape in a cross-sectional view of the housing along a plane including the light source, the first light receiving unit, and the second light receiving unit.

9. The concentration measuring module according to claim 1, wherein the second light receiving unit has an amplifier circuit on an output side of the second light receiving unit, the amplifier circuit being configured to amplify an output of the second light receiving unit, and a distance in a straight line between the center of a photoreceptor of the second light receiving unit and a contact point of a wiring on the first amplifier circuit is 5 cm or less, the wiring connecting the photoreceptor with the first amplifier circuit.

10. The concentration measuring module according to claim 1, wherein the second light receiving unit has an amplifier circuit on an output side of the second light receiving unit, the amplifier circuit being configured to amplify an output of the second light receiving unit, and 90% or more of a solid angle viewed from a center of a wiring from a photoreceptor of the second light receiving unit to the amplifier circuit is covered with a good conductor.

11. The concentration measuring module according to claim 1, wherein the second light receiving unit has an amplifier circuit on an output side of the second light receiving unit, the amplifier circuit being configured to amplify an output of the second light receiving unit, and 90% or more of a solid angle viewed from the center of a wiring from a photoreceptor of the second light receiving unit to the amplifier circuit is covered with a good conductor, and the amplifier circuit is electrically shielded by the good conductor.

12. The concentration measuring module according to claim 1, wherein the irradiated body contains urea and albumin.

13. The concentration measuring module according to claim 12, wherein the first light receiving unit is configured to have sensitivity to a wavelength of light attenuated by urea contained in the irradiated body, of the output light, and the second light receiving unit is configured to have sensitivity to a wavelength of excitation light that albumin contained in the irradiated body radiates by the output light.

14. The concentration measuring module according to claim 1, wherein the light source is a light-emitting diode configured to emit light with a wavelength band of 200 nm or more and 300 nm or less.

15. The concentration measuring module according to claim 1, further comprising an arithmetic logical unit configured to calculate concentration of a constituent contained in the irradiated body on a basis of outputs of the first and second light receiving units.

16. The concentration measuring module according to claim 1, further comprising a control unit configured to control driving of the light source.

17. The concentration measuring module according to claim 16, wherein the control unit is configured to drive the light source so that the output light is emission pulses with a duty ratio of 20% or less.

18. A dialyzer comprising the concentration measuring module according to claim 1.

19. A method of calculating concentrations of two constituents contained in an irradiated body irradiated with output light of a light source by using the concentration measuring module according to claim 1, the method comprising:

acquiring a first signal correlated to an amount of absorption of the output light by the irradiated body;

acquiring a second signal correlated to an amount of excitation of the irradiated body by the output light, the second signal being different from the first signal; and calculating the concentrations of the two constituents on a basis of the first and second signals.

20. The concentration measuring module according to claim 1, wherein the length X of the line segment and the length Y of the line segment satisfy $3.5 \leq Y/(X\textasciicircum 0.2) \leq 12$.

21. The concentration measuring module according to claim 1, wherein the length X of the line segment and the length Y of the line segment satisfy $4.0 \leq Y/(X\textasciicircum 0.2) \leq 10$.

* * * * *